(12) United States Patent
Burns et al.

(10) Patent No.: US 6,298,498 B1
(45) Date of Patent: Oct. 9, 2001

(54) PROTECTIVE HELMET SYSTEM

(75) Inventors: James A. Burns, Lake Elmo; Frank J. Fabin, Eagan; Floyd L. Foslien, Hudson; William A. Mittelstadt, Woodbury, all of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/490,878

(22) Filed: Jan. 24, 2000

Related U.S. Application Data

(62) Division of application No. 09/037,633, filed on Mar. 10, 1998, now Pat. No. 6,035,451.

(51) Int. Cl.$^7$ ...................................................... A42B 1/08
(52) U.S. Cl. ............................................ 2/424; 2/8; 2/6.4
(58) Field of Search ............................. 2/424, 9, 10, 6.3, 2/6.4, 6.5, 6.7, 8, 15

(56) References Cited

U.S. PATENT DOCUMENTS

| | | | |
|---|---|---|---|
| 2,363,461 | * | 11/1944 | Huntsman . |
| 2,406,092 | * | 8/1946 | Meyer . |
| 2,433,164 | * | 12/1947 | Shields . |
| 3,037,236 | * | 6/1962 | Miller . |
| 3,239,843 | * | 3/1966 | Lobelle . |
| 3,582,991 | * | 6/1971 | Metz . |
| 4,170,792 | * | 10/1979 | Higgs . |
| 4,853,973 | * | 8/1989 | Boochard . |
| 5,230,101 | * | 7/1993 | Hedges et al. . |

FOREIGN PATENT DOCUMENTS

| | | |
|---|---|---|
| 25531 | 4/1999 | (ES) . |
| 25532 | 5/1999 | (ES) . |

\* cited by examiner

Primary Examiner—Rodney M. Lindsey
(74) Attorney, Agent, or Firm—Michaele A. Hakamaki

(57) ABSTRACT

A jaw piece is attachable to a base edge of the helmet. The jaw piece and a portion of the base edge of the helmet define a user viewing window. A first face shield is pivotable between an open position and a closed position extending across the viewing window. A seal is provided to engage with a perimeter of the viewing window when the first face shield is in the closed position. The attaching assembly for attaching the first face shield comprises a helmet cam having first helmet cam surfaces configured to releasably attach the first face shield to the protective helmet system and second helmet cam surfaces configured to releasably attach a second face shield to the protective helmet. The attaching assembly generates a first biasing force to bias the seal toward the perimeter of the viewing window when the first face shield is in the closed position.

5 Claims, 10 Drawing Sheets

PROTECTIVE HELMET SYSTEM

This is a divisional of application Ser. No. 09/037,633 filed Mar. 10, 1998 now U.S. Pat. No. 6,035,451.

FIELD OF THE INVENTION

The present invention relates to a protective helmet system convertible between multiple protection classifications.

BACKGROUND OF THE INVENTION

Protective helmets are commonly worn by people to shield their heads from flying or falling objects. The helmet usually has a rigid protective shell of an impact resistant material. For some applications, helmets have face shields attached thereto to protect the wearer's face. The helmet and face shield can form a protective enclosure to which is supplied uncontaminated air. Respirators are frequently combined with helmets and face shields to protect workers in areas where the air may be contaminated by toxic or noxious substances, such as particulates, gases and vapors.

Various government agencies and industry organizations define certain requirements and standards for protective gear, including helmets and respirators. For example, the National Institute of Occupational Safety and Health (NIOSH) certifies certain safety standards in the U.S. The American National Standards Institute (ANSI) recommends voluntary consensus industry standards. Other agencies and organizations around the world also establish safety standards for helmets and respirators. For protective helmets, some of the standards relate to impact energy attenuation, penetration resistance, force transmission, stiffness, flammability, electrical insulation, and head coverage.

The term "loose fitting face piece" defines a ANSI classification of a respiratory protective system in which the respirator enclosure is designed to form a partial seal with the face. Loose fitting face pieces do not seal on the neck and shoulders of the wearer and may or may not offer head protection against impacts and penetration. Positive pressure respiratory air supplied to such a system assists in forming a protective shield around the worker's face. A "loose fitting helmet" is another ANSI classification in which the respirator completely covers the head and neck, and may cover portions of the shoulders. Loose fitting helmets typically seal around the neck of the user. ANSI standards permit the use of "loose fitting face pieces" for exposures of up to 25 times the permissible exposure limit (PEL) for most contaminants. Loose fitting face pieces are typically not worn by users with facial hair. A loose fitting helmet can be used with up to 1,000 times the PEL, and may be used with facial hair.

Some workers may require multiple face pieces attached to a single helmet. Welding operations present a number of potential hazards to the welder that require the welder to use a specially designed protective device. Welding can cause sparks and hot metal debris to fly off the work piece. Welders often wear a clear face shield attached to a helmet to protect their head and face when the welding shield is raised. Welding can also generate toxic or noxious fumes requiring the welder to wear a respiratory system. Welding also causes high intensity light to be generated, requiring the welder to wear a darkened lens over their eyes to prevent eye damage.

Protective systems with the highest level of protection may not be optimum for a particular job that does not require that level of protection. For example, protective systems with a high level of protection can be heavy, may cause some discomfort to the wearer and can be costly. Although a loose fitting face piece system is lighter, less expensive, and more convenient than a loose fitting helmet, such systems are not acceptable for some applications. Therefore, many different types of helmets, respirators and face shields have been developed to meet the many different applications and standards that exist. Consequently, manufacturers have been forced to produce a variety of different systems for different conditions, as well as requiring users to stock and maintain many different systems. There is a need for a protective device that can be convertible between different production classifications.

SUMMARY OF THE INVENTION

The present invention is directed to protective helmet system that can be configured for a variety of protection classifications. The ability to use the same helmet and face shields in multiple respiratory protection classifications reduces the number of different systems that need to be manufactured and reduces the number of components that need to be maintained in inventory. The present invention is also directed to a compact attaching mechanism that permits multiple face shields to be releasably attached to the helmet, either individually or simultaneously. The compact nature of the attaching mechanism provides for tight sealing engagement between the various components of the present protective helmet system.

All of the embodiments of the present invention can be used with a seal extending between the protective helmet system and the user. The seal can form either a loose fitting face piece or a loose fitting helmet. A source of pressurized air is optionally provided to the protective helmet system to form a positive pressure respirator.

In one embodiment, a jaw piece is attachable to a base edge of the helmet. The jaw piece and a portion of the base edge of the helmet define a user viewing window. A first face shield is pivotable between an open position and a closed position extending across the viewing window. A seal is provided to engage with a perimeter of the viewing window when the first face shield is in the closed position. The attaching assembly for attaching the first face shield comprises a helmet cam having first helmet cam surfaces configured to releasably attach the first face shield to the protective helmet system and second helmet cam surfaces configured to releasably attach a second face shield to the protective helmet. The attaching assembly generates a first biasing force to bias the seal toward the perimeter of the viewing window when the first face shield is in the closed position and a second biasing force to bias the first face shield away from the jaw piece when in the open position.

In another embodiment, the protective helmet system comprises a helmet, a first face shield pivotable between an open position and a closed position, and an attaching assembly. The attaching assembly comprises a helmet cam having first helmet cam surfaces extending radially outward from the helmet cam configured to releasably attach the first face shield to the protective helmet system and second helmet cam surfaces extending axially from the helmet cam configured to releasably attach an optional second face shield to the protective helmet. The attaching assembly generates a first biasing force to bias the first face shield seal downward when the first face shield is in the closed position and a second biasing force to bias the first face shield upward when in the open position.

The present invention is also directed to a modular protective helmet system kit for multiple protection classification. A first face shield is optionally attachable to the helmet. The first face shield is pivotable between an open position and a closed position extending across a viewing window when attached to the helmet. A second face shield is optionally attachable to the helmet. The second face shield is configured to extend over the first face shield and substantially across the viewing window when attached to the helmet. The attaching mechanism includes first helmet cam surfaces configured to releasably attach the first face shield to the protective helmet system and second helmet cam surfaces configured to releasably attach the second face shield to the protective helmet. The attaching assembly generates a downward biasing force when the first face shield is in the closed position and an upward biasing force when the face shield is in the open position.

An extender having a neck seal is optionally attachable to a base edge of the first face shield. In an alternate embodiment, a jaw piece having a sealing surface is optionally attached to a base edge of the helmet. A seal is provided to engage with the sealing surface when the first face shield is in the closed position.

DETAILED DESCRIPTION OF THE INVENTION

Figure 1:
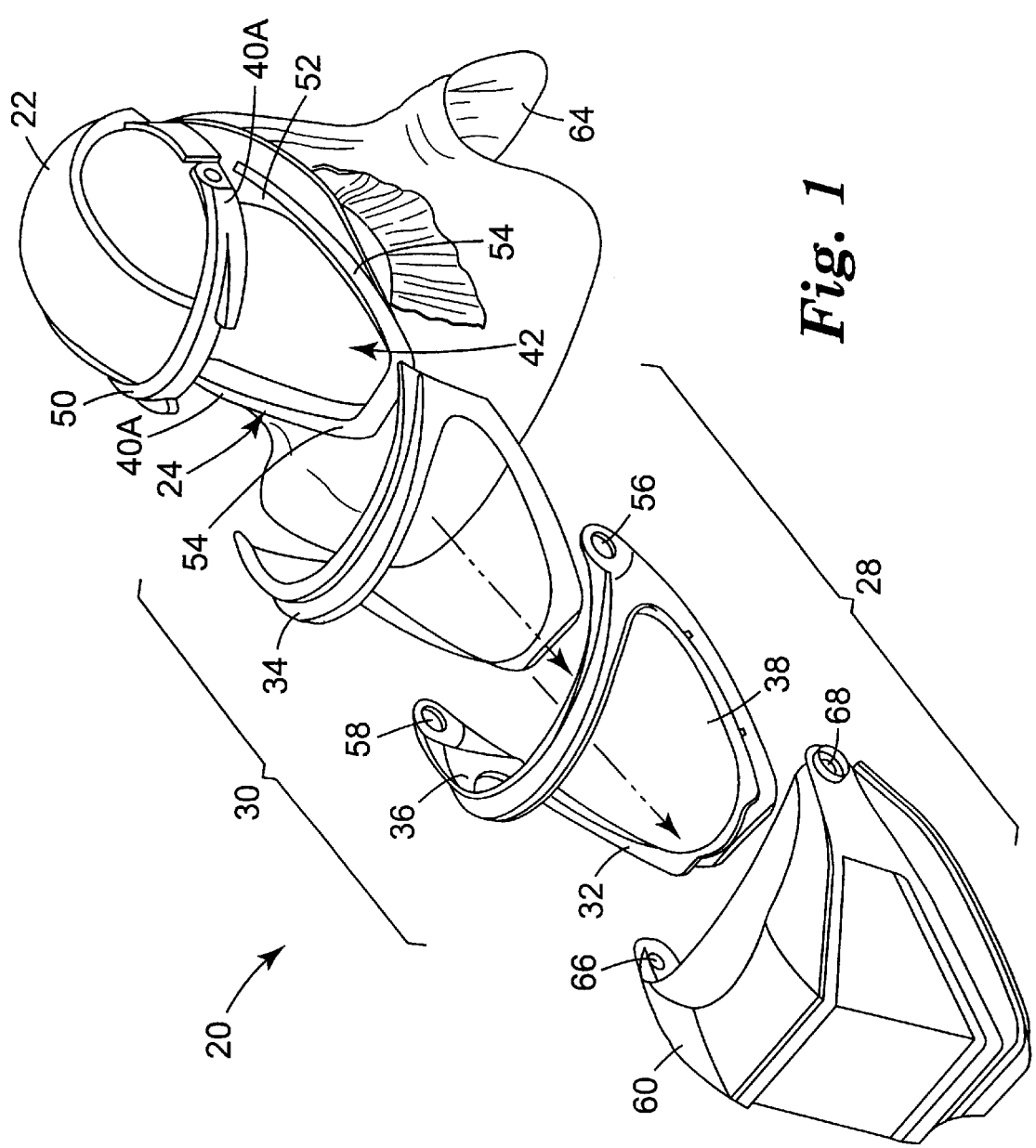
FIG. 1 is an exploded perspective view of a protective helmet system in accordance with the present invention.

FIG. 1 is a perspective view of a protective helmet system 20 including a helmet 22 in accordance with the present invention. Helmet 22 can be a simple bump cap (such as defined in European standard CEN EN 812) or a hard hat meeting more stringent protection classifications (such as defined in ANSI Z89. 1-1997). Protective lens system 28 illustrates a variety of protective lenses that can be releasably attached to the helmet 22. The helmet 22 can be used alone or in combination with a jaw piece 24 to form a protective enclosure 26 around the user's face (not shown). The jaw piece 24 is preferably rigidly attached to the helmet 22. The jaw pieces 24 provide registration and sealing surfaces 52, 54 for the various components of the protective lens system 28. An extender 61 having a face seal 62 can optionally be attached to one of the components of the protective lens system 28 to form the protective enclosure around the user's face (see FIG. 4).

Wide view lens face shield 30 includes a wide view frame 32 having an elastomeric peripheral seal 34 along an inner surface 36. A transparent wide view lens 38 is releasably mounted within the wide view frame 32, as discussed in commonly assigned U.S. patent application Ser. No. 09/037, 628 entitled "Attachment System For Replaceable Helmet Respirator Lens," filed on the same date herewith. The wide view lens face shield 30 is configured to extend around a perimeter 40A of a viewing window 42 formed between the helmet 22 and the jaw piece 24, or a perimeter 40B of the viewing window 42 formed between the helmet 22 and the extender 61 (see FIG. 4). The elastomeric peripheral seal 34 is configured to engage with a first sealing surface 50 along an upper edge of the helmet 22 and the second and third sealing surfaces 52, 54 located on the jaw piece 24 (see FIG. 9). The seal 34 may also form a sealing engagement with the extender 61. The wide view frame 32 includes mounting holes 56, 58 for pivotal attachment to the helmet 22 as will be discussed in detail below.

Welding shield 60 may be pivotally attached to the helmet 22, either alone or in combination with the wide view lens face shield 30. The welding shield includes mounting holes 66, 68 for rotational attachment to the helmet 22. The protective helmet system 20 may optionally include a shroud 64 configured to extend over the user's shoulders. The shroud 64 is typically attached to the jaw piece 24 and a base edge 70 of the helmet 22. In an alternate embodiment illustrated in FIG. 4, the extender 61 has a face seal 62 that extends between the protective helmet system 20 and the user. The shroud 64 or face seal 62 used in combination with a source of pressurized air permits the present protective helmet system 20 to form a positive pressure respirator.

Figure 2:
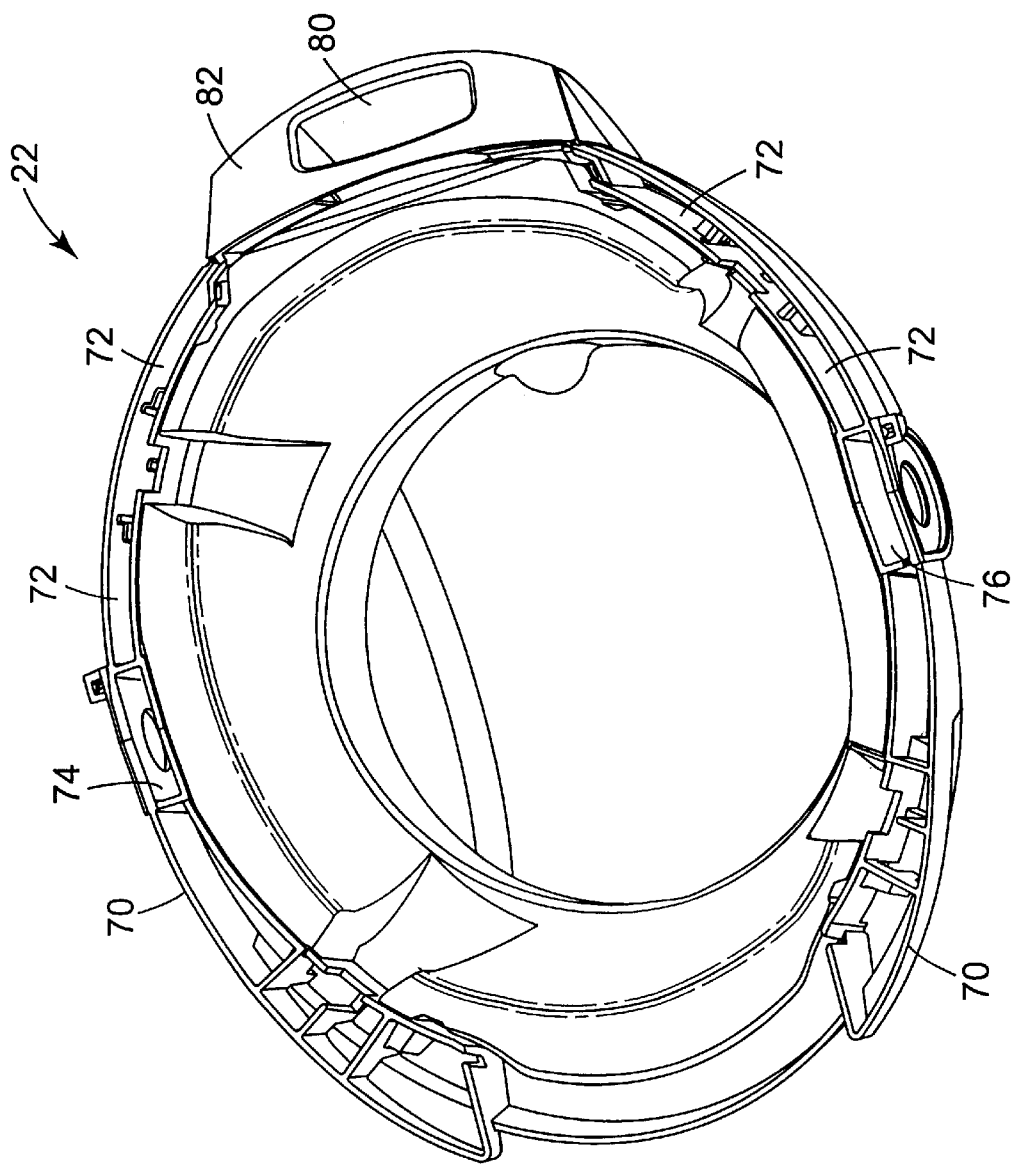
FIG. 2 is a bottom view of a helmet suitable for use in the present protective helmet system.
Figure 3:
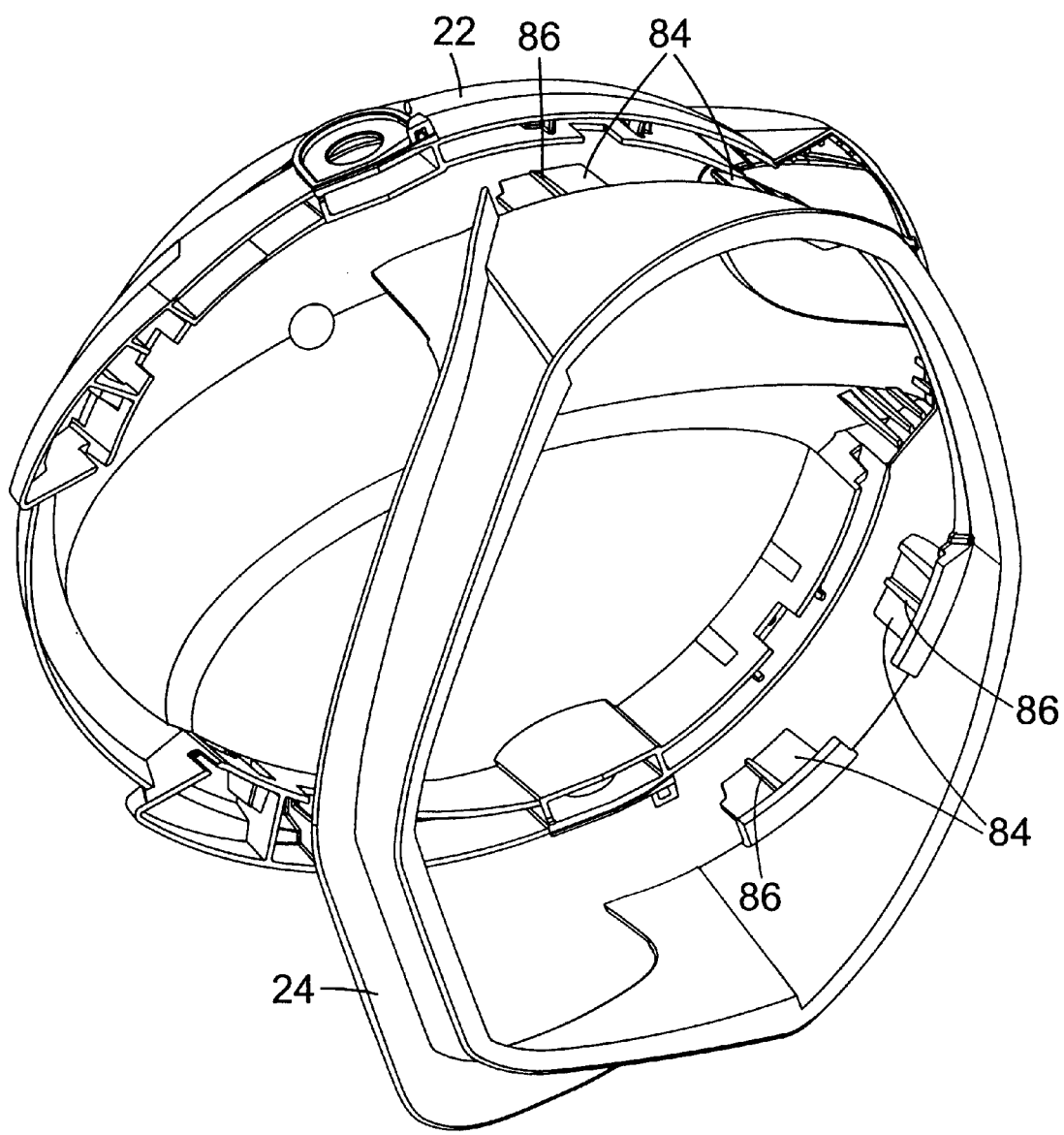
FIG. 3 is a perspective view of a combination helmet and jaw piece in accordance with the present protective helmet system.

FIG. 2 is a bottom perspective view of the base edge 70 of the helmet 22 having a plurality of jaw piece mounting slots 72 arranged for engagement with the jaw piece 24 (see FIG. 3). The base edge 70 also includes a pair of helmet cam clip housings 74, 76 for releasably mounting an attaching assembly 78 to the helmet 22 (see FIG. 4). Pressure port 80 is provided at a rear edge 82 of the helmet 22 for attachment to a source of pressurized air (not shown) to form an atmosphere supplied device, also known as a positive pressure respirator. The source of pressurized air assists in maintaining a net flow of air out from the protective enclosure 26, thereby minimizing the chance that contaminant will penetrate into the protective enclosure 26.

FIG. 3 is a perspective view of the helmet 22 in the process of being engaged to the jaw piece 24. The jaw piece 24 includes a series of connector members 84 configured to engage with the jaw piece mounting slot 72 along the base edge 70 of the helmet 22. The connector members 84 preferably include compression ribs 86 to ensure a tight fit between the jaw piece 24 and the helmet 22. Attachment of the jaw piece 24 to the helmet 22 converts a loose fitting face piece system into a loose fitting helmet construction. In one embodiment of the present invention, the jaw piece 24 is releasably attached to the helmet 22. Alternatively, the jaw piece 24 may be permanently adhered to the helmet 22 using a suitable adhesive.

Figure 4:
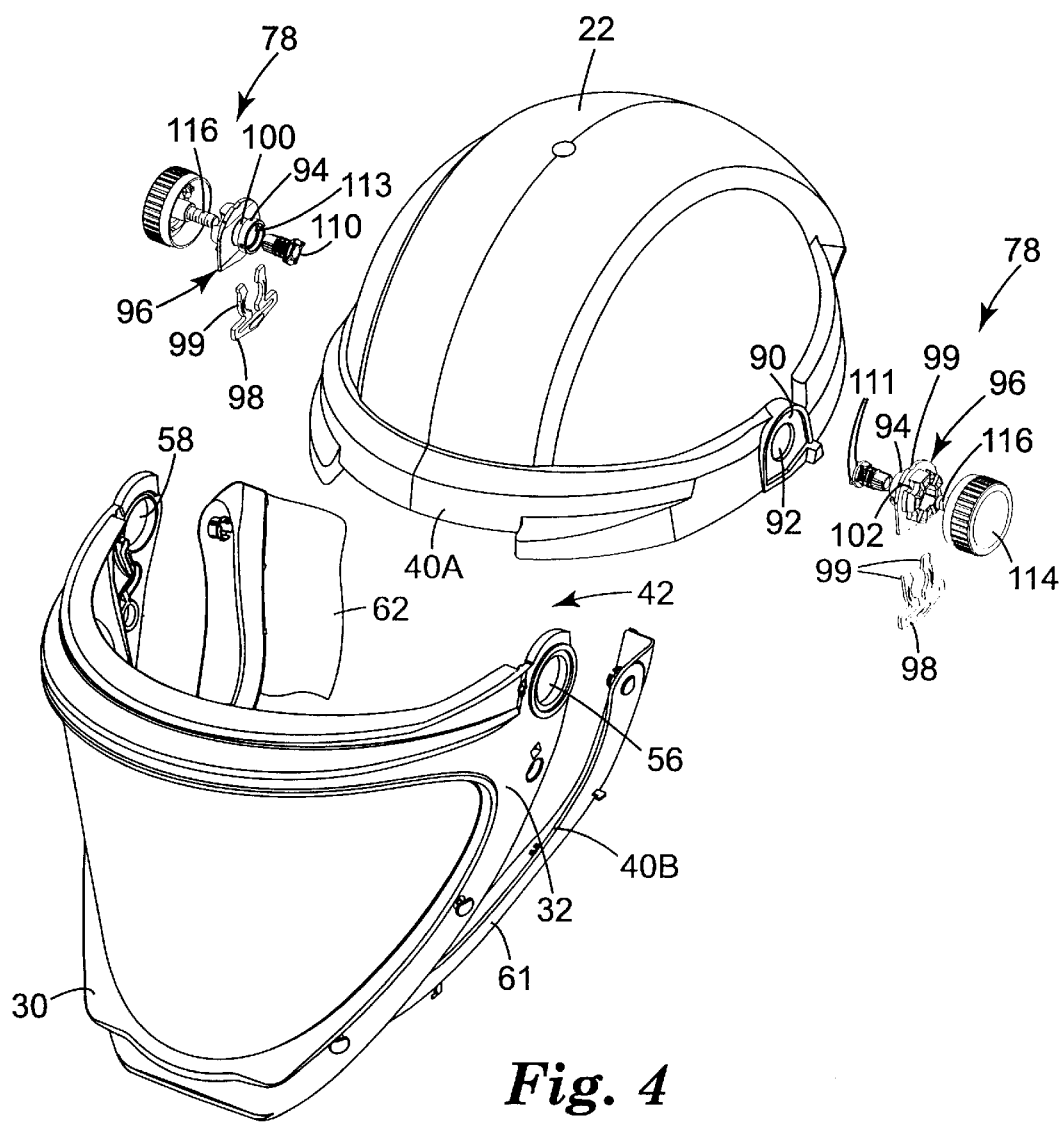
FIG. 4 is a perspective view of an attaching assembly for use in the present protective helmet system.
Figure 5:
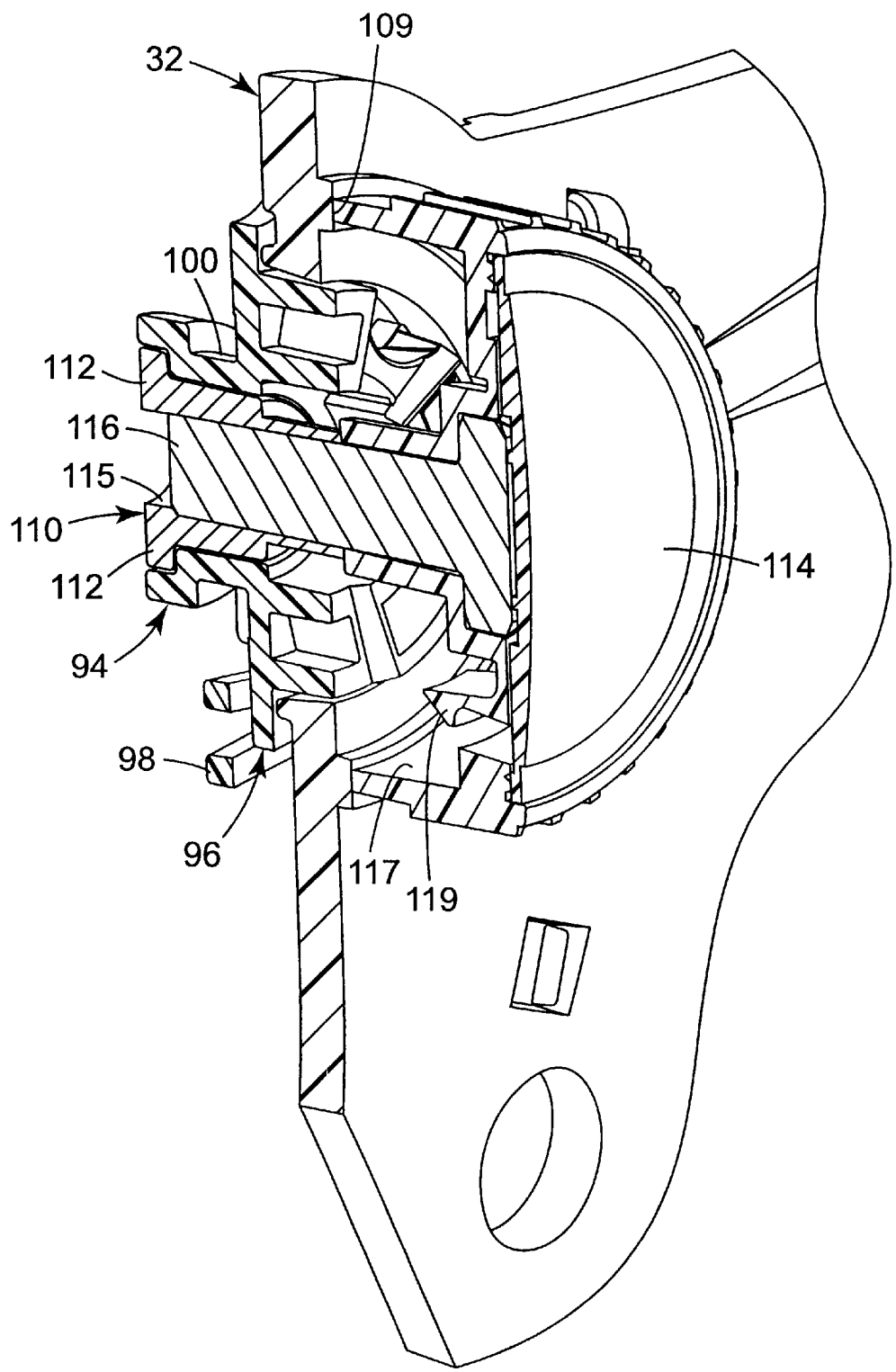
FIG. 5 is a sectional view of the attaching assembly of FIG. 4.

FIGS. 4 and 5 illustrate the engagement of the attaching assembly 78 to wide view frame 32 of the face shield 30 to the helmet 22. The helmet 22 includes a helmet cam recess 90 having a hole 92 for receiving an elongated portion 94 on a helmet cam 96. The helmet cam 96 is preferably symmetrical so that it can be used on either side of the helmet 22. Once the elongated portion 94 is engaged with the hole 92, a helmet cam clip 98 is inserted through the helmet cam clip housing 74 (see FIG. 2) that compressibly engages with a slot 100 on the helmet cam 96. The helmet cam 96, helmet cam clip 98, and weld cam 102 (see FIG. 11) preferably includes compression ribs 99 to form an interference fit with the mating component.

Pivot post 110 having a flange 112 is inserted through the rear of the helmet cam 96 for engagement with a knob assembly 114. The pivot post 110 preferably has an internally threaded portion 115 for engagement with a threaded member 116 on the knob assembly 114. Surface 109 on the knob assembly 114 retains the frame 32 to the helmet cam 96. In one embodiment, the pivot post 110 also includes tabs 111 configured to engage with slots 113 on the helmet cam 96 to prevent rotation of the pivot post 110 during engagement with the knob assembly 114. The knob assembly 114 preferably defines a recess 117 having tabs 119 for optionally retaining a spring 172 (see FIG. 8), as will be discussed below.

Figure 6:
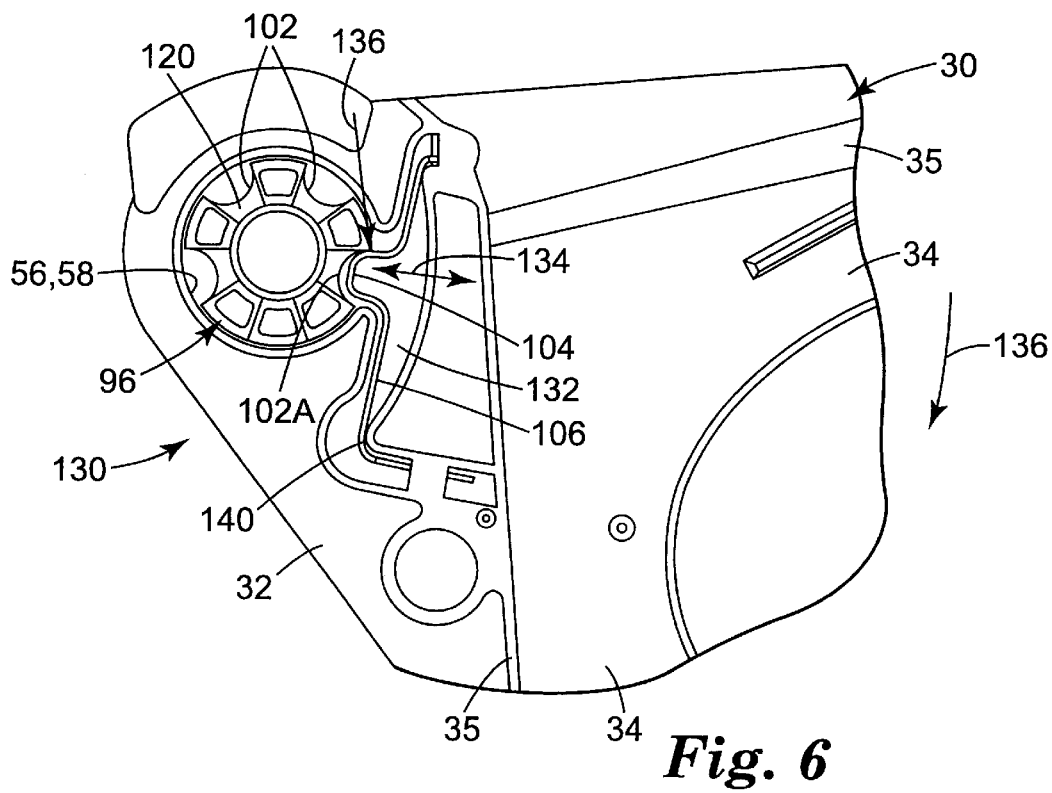
FIG. 6 illustrates engagement of the attaching assembly with a face shield in the closed position.
Figure 7:
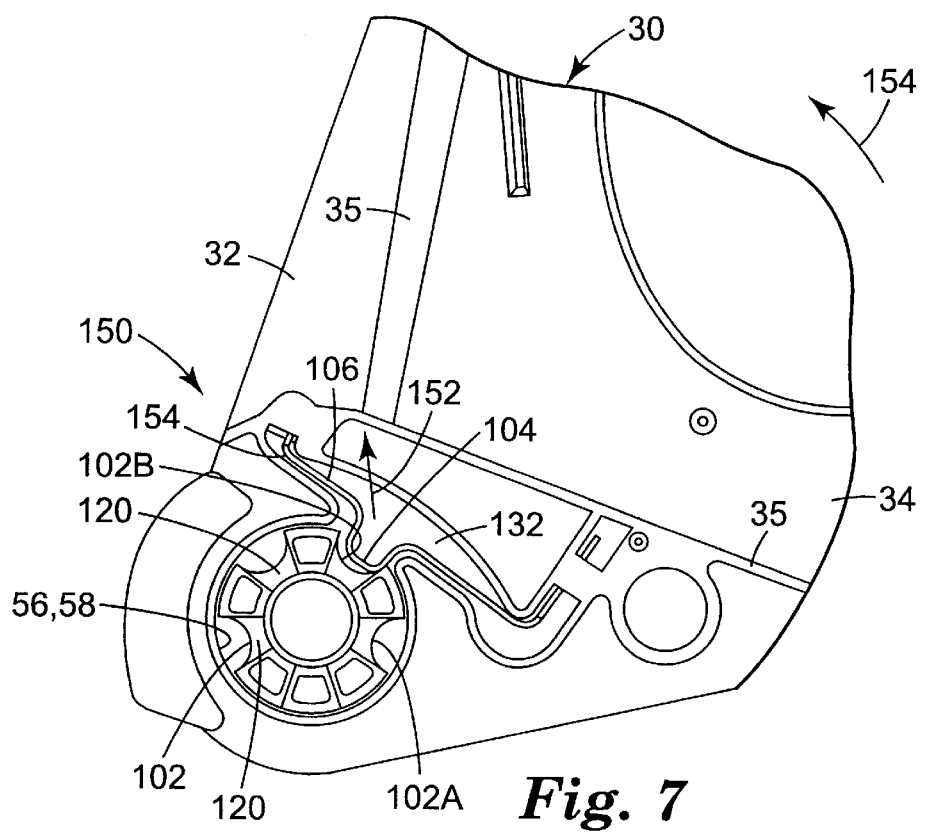
FIG. 7 illustrates engagement of the attaching assembly with a face shield in the opened position.

As best seen in FIGS. 6 and 7, the exposed side of the helmet cam 96 includes a plurality of radial cam surfaces 102 that are positioned to engage radially with a cam engaging surface 104 of a spring 106 located on the wide view frame 32 adjacent to the holes 56, 58. In addition to the radial cam surfaces 102, the helmet cam 96 includes a series of axial cam surfaces 120 for engagement with corresponding axial cam surfaces 122 on a second face shield cam 124 (see FIG. 11).

FIG. 6 is a plane view of an inside edge of the wide view frame 32 of the face shield 30 engaged with the helmet cam 96 in a closed position 130. The spring 106 is mounted in a recess 132 to permit flexure along a spring axis 134. In the closed configuration 130 illustrated in FIG. 6, the cam engaging surface 104 is not fully engaged with the radial cam surface 102A, so as to create a downward biasing force 136. The biasing force 136 creates a slight separation of the spring 106 from the recess structure 132 at the location 140. The net effect of the biasing force 136 is to bias the peripheral seal 34 toward the perimeter 40 of the viewing window 42 (see FIG. 1). Also seen in FIG. 6 are raised portions 35 on the peripheral seal 34 configured for engaging with the perimeter 40 of the viewing window 42 when the face shield 30 is in the closed position 130.

FIG. 7 illustrates the wide view lens face shield 30 biased in an open position 150. The radial cam surface 102B is slightly offset from the cam engaging surface 104 of the spring 106 so as to create an upward biasing force 152. The biasing force 152 creates a slight separation between the spring 106 and the recess structure 132 at the location 154.

Figure 8:
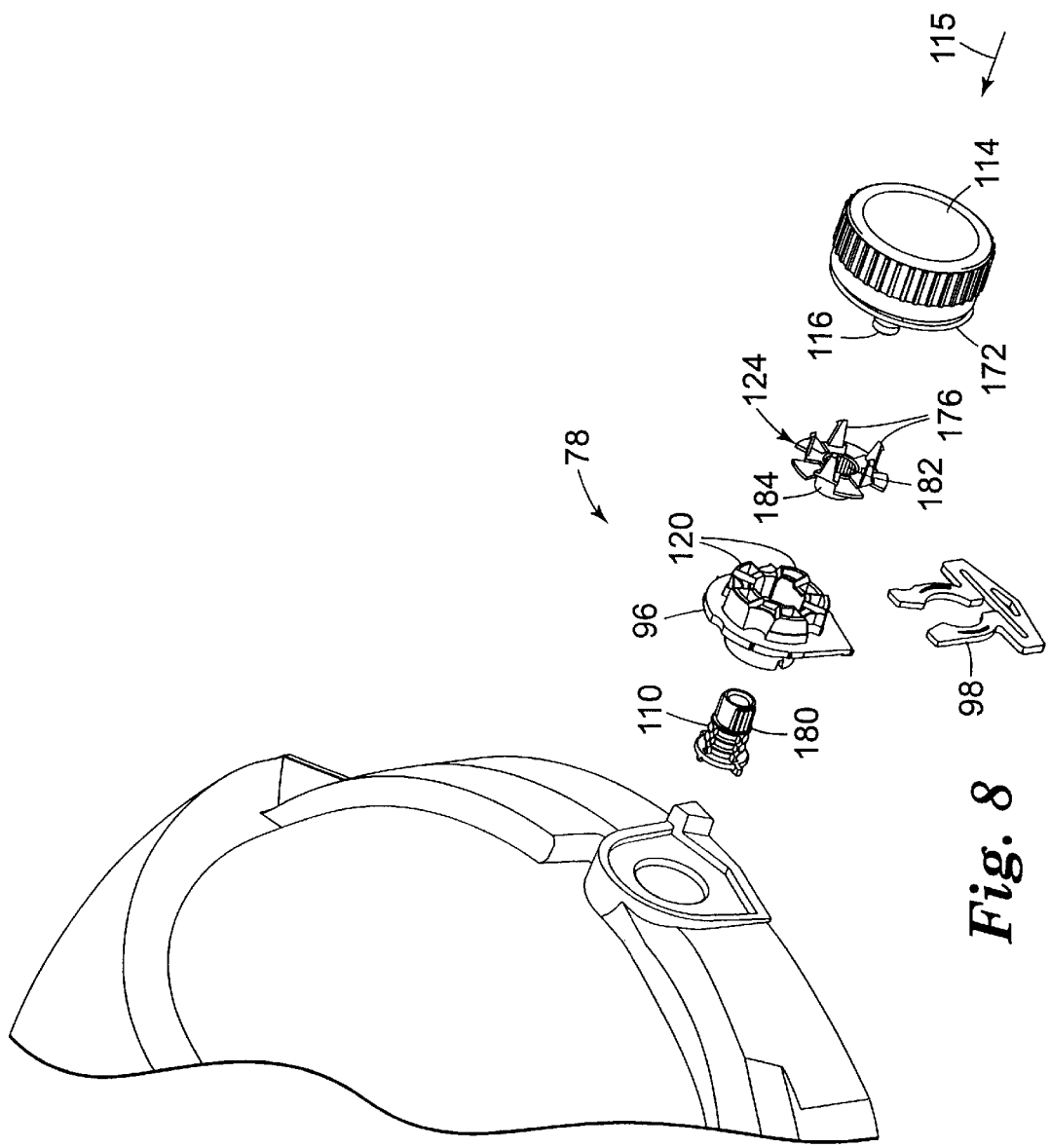
FIG. 8 is a perspective view of a modified attaching assembly for use in the present protective helmet system.
Figure 9:
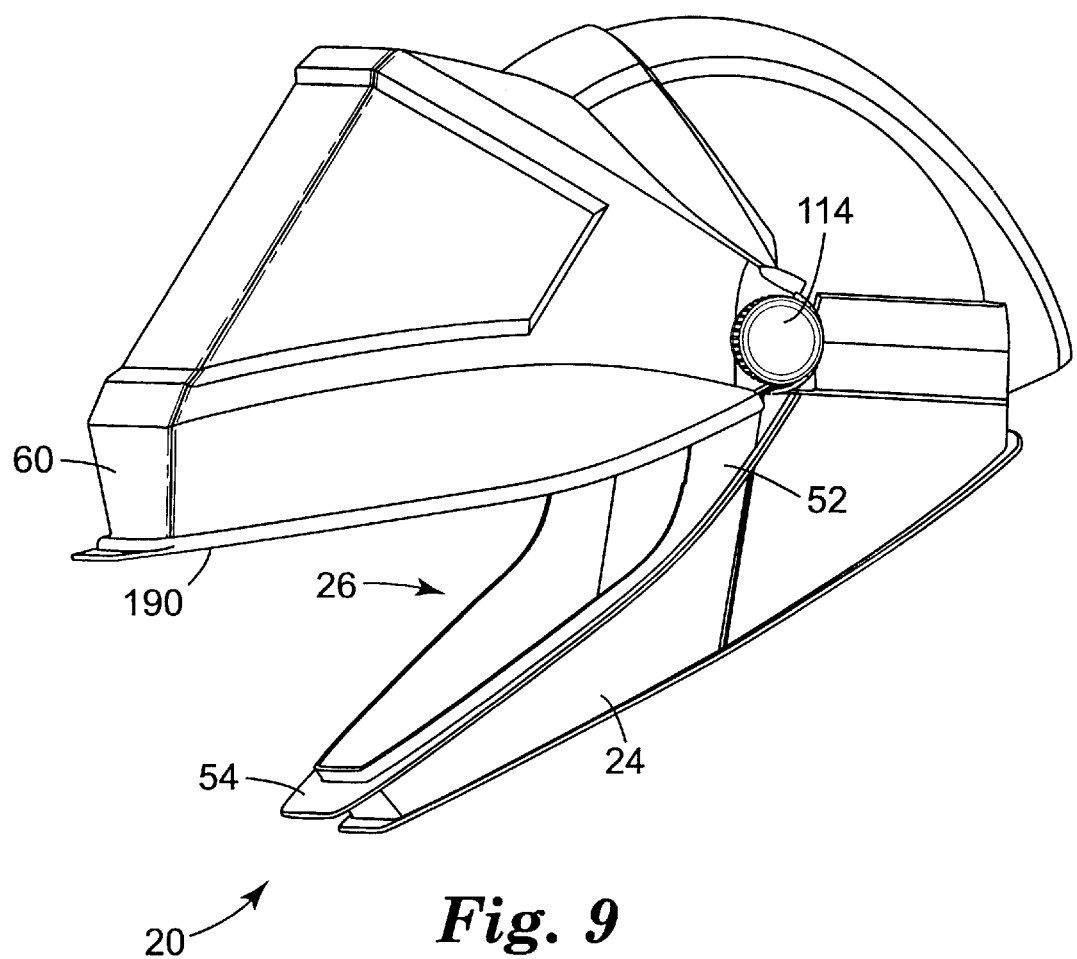
FIG. 9 is a perspective view of a second face shield on the protective helmet system in accordance with the present invention.

FIGS. 8 through 11 illustrate use of the attaching assembly 78 to include a second face shield 60, such as the welding shield illustrated in FIG. 9, to the present protective helmet system 20. The knob assembly 114 is slightly modified to include a spring 172 to provide a bias between the second face shield cam surfaces 122 and the axial cam surfaces 120 located on the helmet cam 96. In the embodiment illustrated in FIG. 8, the second face shield cam 124 is illustrated as a component separate from the second face shield 60. Attachment tabs 176 are preferably included for releasable engagement with the second face shield 60 (see FIG. 10). Alternatively, the cam surfaces 122 can be integrally formed on the second face shield 60.

In the embodiment illustrated in FIG. 8, the pivot post 110 includes spline teeth 180 positioned to engage with corresponding spline teeth 182 on an inside surface of hole 184 on the second face shield cam 124. Consequently, the pivot post 110 does not rotate when the threaded member 116 of the knob assembly 114 is engaged with the pivot post 110 to generate all axial compressive force 115. Once the cam surfaces 120, 122 are compressively engaged by the axial compressive force 115, the second face shield cam 124, pivot post 110 and knob assembly 114 rotate with the second face shield 60.

Figure 10:
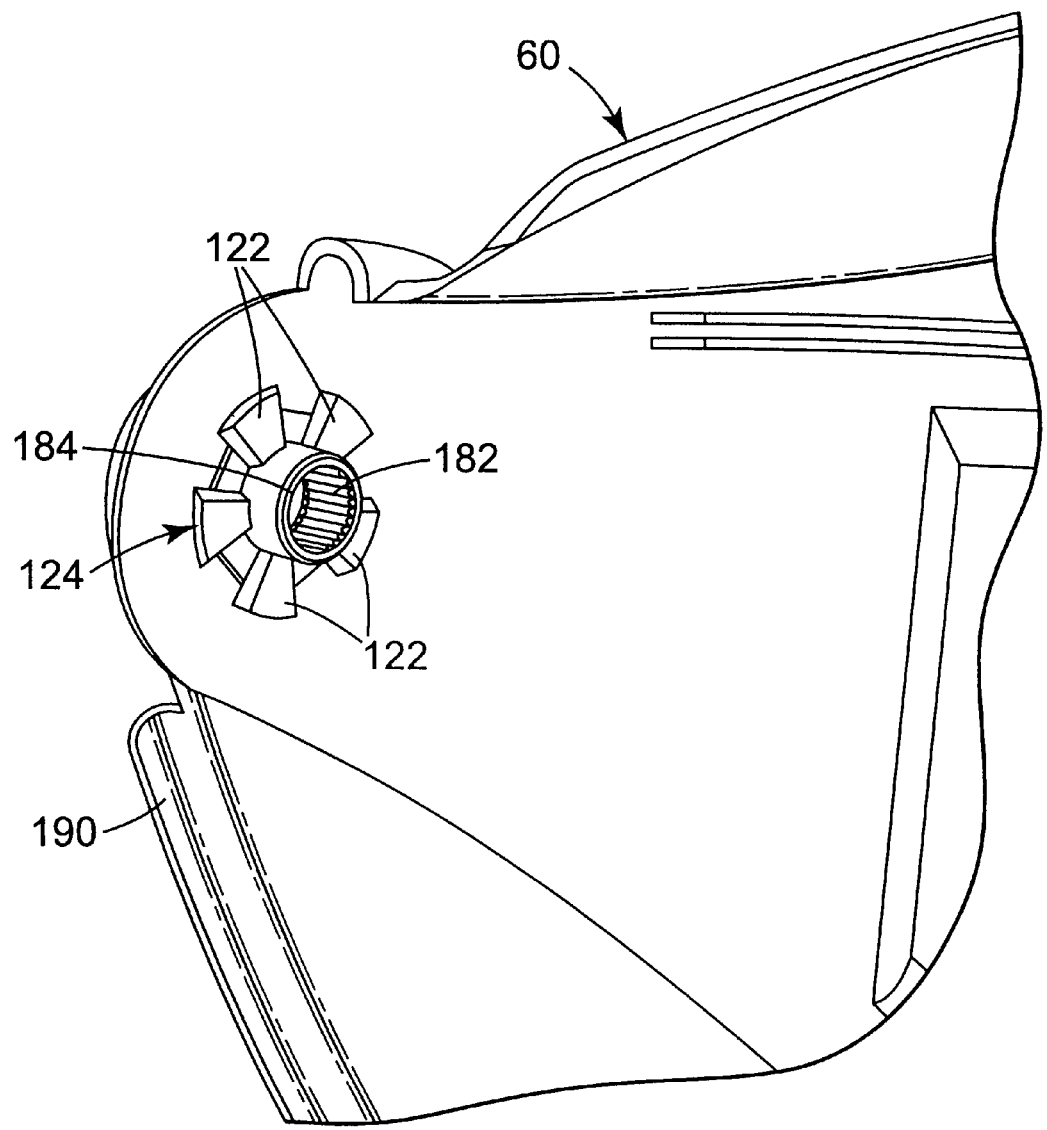
FIG. 10 is a perspective view of an interface on the second face shield for use with the attaching assembly.

As best illustrated in FIGS. 9 and 10, the third sealing surface 54 on the jaw piece 24 comprises a ridge configured to engage with an L-shaped lip 190 on the second face shield 60. The combination of ridge 54 and L-shaped lip 180 creates a tortuous path that minimizes the penetration of direct and indirect radiation into the enclosure 26.

Figure 11:
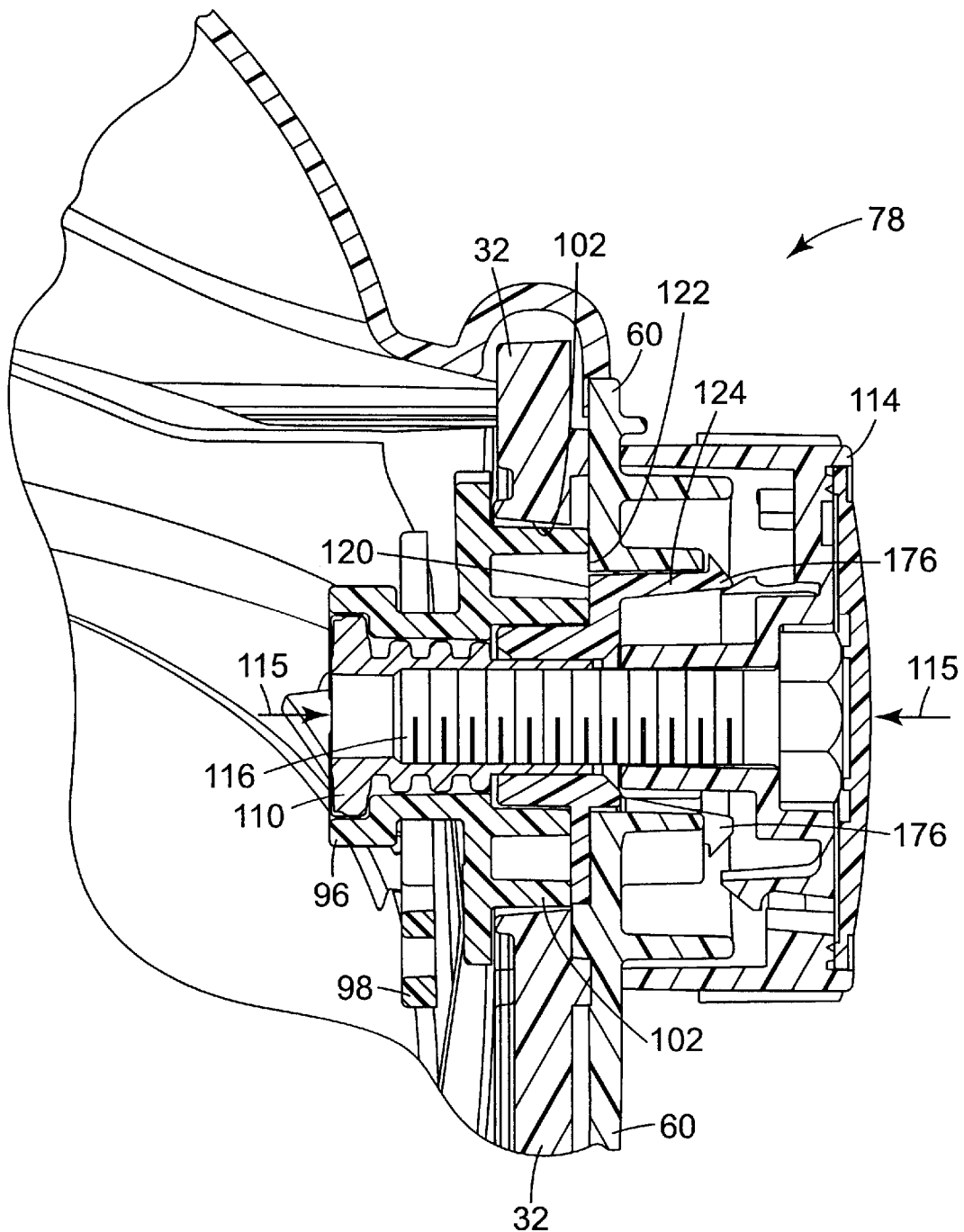
FIG. 11 is a sectional view of the attaching assembly of FIG. 8.

As best seen in FIG. 11, the wide view frame 32 engages with the radial cam surfaces 102 and the second face shield 60 engages with the axial cam surfaces 120 on the helmet cam 96. Consequently, the attaching assembly 78 is extremely compact, permitting the wide view lens face shield 30 and second face shield 60 to be releasably attached with minimal offsets from the helmet 22. That is, the attaching assembly 78 provides a tight sealing engagement between the wide view lens face shield 30, the second face shield 60 and the helmet 22, thereby maximizing sealing capabilities of the system 20.

The present protective helmet system 20 can be arranged in a variety of configurations. In a first set of configurations, a bump cap helmet 22 and the extender 61 (and face seal 62) can be configured with the wide view lens face shield 30, the welding shield 60, or both. Pressurized air is supplied to the loose fitting face piece to form a positive pressure respirator suitable for exposures of up to 25 times the permissible exposure limit (PEL) for most contaminants. In a second set of configurations, a hard hat is substituted for the bump cap. In a third set of configurations, the shroud 64 and jaw piece 24 are attached to the hard hat helmet 22 to form a loose fitting helmet. The loose fitting helmet can be configured with the face shield 30, welding shield 60, or both. Pressurized air is supplied to the loose fitting helmet to form a positive pressure respirator configuration suitable for exposures of up to 1000 times the permissible exposure limit (PEL) for most contaminants. In a fourth set of configurations, the present protective helmet system 20 can be used without a source of pressurized air, preferably without the face seal 62 or shroud 64.

The complete disclosures of all patents, patent applications, and publications are incorporated herein by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A protective helmet system, comprising:
   a helmet having a base edge;
   a jaw piece attachable to the base edge of the helmet comprising a sealing surface, the jaw piece and a portion of the base edge of the helmet defining a user viewing window;
   a first face shield pivotable between an open position and a closed position extending across the viewing window;

a seal configured to engage with a perimeter of the viewing window when the first face shield is in the closed position; and an attaching assembly comprising a helmet cam having first helmet cam surfaces configured to releasably attach the first face shield to the protective helmet system and second helmet cam surfaces configured to releasably attach a second face shield to the protective helmet, the attaching assembly generating a first biasing force to bias the seal toward the perimeter of the viewing window when the first face shield is in the closed position and a second biasing force to bias the first face shield away from the jaw piece when in the open position; and a second face shield releasably engaged with the second helmet cam surfaces.

2. The system of claim 1 wherein the second face shield comprises second face shield cam surfaces positioned to axially engage with the second helmet cam surfaces.

3. The system of claim 2 wherein the attaching assembly comprises an adjustable compression mechanism to maintain the second face shield cam surfaces in a compressive engagement with the second helmet cam surfaces.

4. The system of claim 1 wherein the second face shield comprises a welding shield.

5. The system of claim 1 wherein the second face shield comprises a welding shield having an L-shaped lip configured to engage with the sealing surface on the jaw piece, whereby the engagement of the L-shaped lip and the sealing surface defines a circuitous path that minimizes the transmission of light past the perimeter of the viewing window.

* * * * *

UNITED STATES PATENT AND TRADEMARK OFFICE
CERTIFICATE OF CORRECTION

PATENT NO.       : 6,298,498 B1
APPLICATION NO.  : 09/490878
DATED            : October 9, 2001
INVENTOR(S)      : James A. Burns It is certified that error appears in the above-identified patent and that said Letters Patent is hereby corrected as shown below:

Title Page,
References Cited, under U.S. Patent Documents, please add:

| | | |
|---|---|---|
| D 416,649 | 11/16/99 | Burns et al. |
| D 420,770 | 2/15/2000 | Burns |
| D 420,771 | 2/15/2000 | Burns |
| D 421,820 | 3/21/2000 | Johnson |
| 3,067,426 | 12/11/62 | Tompkins |
| 3,375,529 | 4/2/68 | Timm et al. |
| 3,629,868 | 12/28/71 | Greenlee |
| 3,649,964 | 3/21/72 | Schoetz et al. |
| 3,945,043 | 3/23/76 | DeAngelis |
| 4,040,123 | 8/9/77 | Williams |
| 4,109,320 | 8/29/78 | Anderson |
| 4,172,294 | 10/30/79 | Harris |
| 4,183,101 | 1/15/80 | Melander |
| 4,224,694 | 9/30/80 | Palmaer |
| 4,293,757 | 10/6/81 | Niemi |
| 4,536,892 | 8/27/85 | Brinkhoff et al. |
| 4,856,109 | 8/15/89 | Desy et al. |
| 5,054,479 | 10/8/91 | Yelland et al. |
| 5,086,515 | 2/11/92 | Giuliano |
| 5,140,707 | 8/25/92 | Johnson |
| 5,239,703 | 8/31/93 | Nordin et al. |
| 5,549,104 | 8/27/96 | Crump et al. |
| 6,016,805 | 1/25/2000 | Burns et al. |

Under Foreign Patent Documents, please add:

| | | |
|---|---|---|
| 7035512 | 3/4/71 | Germany |
| DE 29 13 059 A1 | 10/9/80 | Germany |
| 25531 | 4/26/99 | Spain |
| 25532 | 5/21/99 | Spain |
| 2 153 003 A | 8/14/85 | United Kingdom |
| 1266818 | 3/15/72 | United Kingdom |
| 2024000A | 1/9/80 | United Kingdom |
| WO 99/45807 | 9/16/99 | WIPO |
| WO 99 45809 | 9/16/99 | WIPO |
| WO 99/46006 | 9/16/99 | WIPO |

UNITED STATES PATENT AND TRADEMARK OFFICE
CERTIFICATE OF CORRECTION

PATENT NO. : 6,298,498 B1
APPLICATION NO. : 09/490878
DATED : October 9, 2001
INVENTOR(S) : James A. Burns It is certified that error appears in the above-identified patent and that said Letters Patent is hereby corrected as shown below:

Under Other Publications, please add:
Product information: *3M Positive Pressure Respirators*, 3M Occupational Health and Environmental Safety Division, December, 1996.
Standard: "American National Standard Practice for Occupational and Educational Eye and Face Protection," American National Standards Institute, Inc., (Approved February 2, 1989).
Brochure: "Powered Respirators," Racal Health & Safety, (undated).

Column 6,
Line 7, "all" should read as --an--.

Signed and Sealed this

Twenty-fifth Day of March, 2008

JON W. DUDAS
*Director of the United States Patent and Trademark Office*